United States Patent
Ao et al.

(10) Patent No.: US 9,343,055 B2
(45) Date of Patent: May 17, 2016

(54) FLUID DENSITY STRATIFICATION LOCATION SYSTEM, DEVICE AND METHOD

(71) Applicant: General Electric Company, Schenectady, NY (US)

(72) Inventors: Xiaolei Shirley Ao, Lexington, MA (US); Shawn Li Doria, North Billerica, MA (US); Jin Chang Xu, Andover, MA (US); Reuben Micah Aronson, Alexandria, VA (US)

(73) Assignee: General Electric Company, Schenectady, NY (US)

( * ) Notice: Subject to any disclaimer, the term of this patent is extended or adjusted under 35 U.S.C. 154(b) by 356 days.

(21) Appl. No.: 13/888,828

(22) Filed: May 7, 2013

(65) Prior Publication Data
US 2014/0331785 A1 Nov. 13, 2014

(51) Int. Cl.
| | |
|---|---|
| *G01F 1/20* | (2006.01) |
| *G10K 11/00* | (2006.01) |
| *G01N 29/024* | (2006.01) |
| *G01N 29/24* | (2006.01) |
| *G01N 29/32* | (2006.01) |
| *G01F 1/66* | (2006.01) |
| *G01F 1/74* | (2006.01) |
| *G01N 9/24* | (2006.01) |

(52) U.S. Cl.
CPC ............... *G10K 11/00* (2013.01); *G01F 1/662* (2013.01); *G01F 1/667* (2013.01); *G01F 1/74* (2013.01); *G01N 29/024* (2013.01); *G01N 29/2462* (2013.01); *G01N 29/326* (2013.01); *G01N 9/24* (2013.01); *G01N 2291/02818* (2013.01); *G01N 2291/02836* (2013.01); *G01N 2291/02881* (2013.01); *G01N 2291/045* (2013.01); *G01N 2291/0426* (2013.01)

(58) Field of Classification Search
CPC .................................. G01F 1/66; G10K 11/00
USPC ...................................................... 73/861.18
See application file for complete search history.

(56) References Cited

U.S. PATENT DOCUMENTS

| | | | |
|---|---|---|---|
| 3,540,265 A * | 11/1970 | Lynnworth | G01N 29/11 374/119 |
| 4,893,496 A | 1/1990 | Bau et al. | |
| 5,036,703 A * | 8/1991 | Eriksson | 73/290 V |
| 5,121,340 A * | 6/1992 | Campbell et al. | 702/54 |

(Continued)

FOREIGN PATENT DOCUMENTS

| | | |
|---|---|---|
| EP | 0384373 A1 | 8/1990 |
| GB | 2270160 A | 3/1994 |

(Continued)

OTHER PUBLICATIONS

International Search Report and Written Opinion issued in connection with corresponding PCT Application No. PCT/US2014/033767 on Aug. 21, 2014.

*Primary Examiner* — Hezron E Williams
*Assistant Examiner* — Tarun Sinha
(74) *Attorney, Agent, or Firm* — Barclay Damon, LLP (57) ABSTRACT

A fluid flow system, device, and method for locating a fluid layer in a fluid flow using an acoustic waveguide. The acoustic waveguide comprises a waveguide base segment, and a waveguide reflector segment. The waveguide reflector segment comprises a plurality of disc shaped waveguide reflectors along its length for locating a fluid layer.

18 Claims, 4 Drawing Sheets

(56) References Cited

U.S. PATENT DOCUMENTS

| | | | |
|---|---|---|---|
| 5,357,801 A * | 10/1994 | Sinclair | 73/290 V |
| 5,900,535 A * | 5/1999 | Doe | 73/32 A |
| 6,889,552 B2 | 5/2005 | Nguyen et al. | |
| 2006/0211128 A1 | 9/2006 | Johnson et al. | |
| 2013/0146388 A1 * | 6/2013 | Ao | G01N 29/2462 181/175 |
| 2014/0331785 A1 * | 11/2014 | Ao et al. | 73/861.18 |

FOREIGN PATENT DOCUMENTS

| | | |
|---|---|---|
| GB | 2309524 A | 7/1997 |
| WO | 9119191 A2 | 12/1991 |

* cited by examiner

FLUID DENSITY STRATIFICATION LOCATION SYSTEM, DEVICE AND METHOD

BACKGROUND OF THE INVENTION

The subject matter disclosed herein relates to an acoustic waveguide, in particular, to an acoustic waveguide having multiple waveguide reflectors for detecting fluid density stratification in a vessel or conduit.

Acoustic waveguides can be used to measure the physical properties (e.g., density, viscosity, level, temperature, etc.) of a fluid flowing or stored in a conduit or vessel. In a typical acoustic waveguide, a transducer assembly launches an acoustic pulse from one end of the waveguide located outside of a sealed conduit while its major portion is submersed into the fluid inside the conduit. The speed of the acoustic pulse in the section of the waveguide submersed into the fluid depends on the physical properties of the fluid and therefore can be used to determine those properties.

One of the physical properties of interest is density of the fluid and its stratification inside a conduit. The conduit can be as large as 12 feet in one dimension, such as diameter or height, in which the density distribution of the sealed fluid can be measured by the waveguide in the form of an elongated rod. Knowledge of the actual density of a fluid at various heights can be used to detect interfaces between 2 different fluids such as a rag layer between oil and water in oil production. The knowledge of the location and thickness of the rag layer inside a conduit such as a desalter enables control over the size of the layer and therefore control over optimizing the oil production process.

The discussion above is merely provided for general background information and is not intended to be used as an aid in determining the scope of the claimed subject matter.

BRIEF DESCRIPTION OF THE INVENTION

By forming multiple waveguide reflectors in an acoustic waveguide at predetermined locations, i.e. at predetermined known distances, the times of flight of the acoustic waves reflected from the various waveguide reflectors allows the physical properties of the fluid to be determined as well as the location of fluid layers (i.e., a depth) in the fluid. The overall speed of the acoustic waves through the waveguide determines the measured times of flight.

A fluid density stratification location system, device, and method for using an elongated acoustic waveguide are disclosed. The acoustic waveguide comprises a waveguide base segment, and a waveguide reflector segment. The waveguide reflector segment comprises a plurality of disc shaped waveguide reflectors spaced apart along its length perpendicular to an axis of the waveguide reflector segment. An advantage that may be realized in the practice of some disclosed embodiments of the multi-reflector acoustic waveguide is enabling determination of the size and location of different layers in a fluid.

In one embodiment, an elongated acoustic waveguide includes a waveguide base segment and a waveguide reflector segment. The waveguide reflector segment includes disc shaped waveguide reflectors spaced apart along its length. The reflector discs are perpendicular to an axis of the waveguide reflector segment.

In another embodiment, a fluid flow system has a pipe with fluid flowing through it. A first acoustic waveguide extends at least into a portion of the flowing fluid. The waveguide has a base segment, and a reflector segment with spaced apart disc shaped waveguide reflectors. The waveguide reflectors are perpendicular to an axis of the reflector segment, and at least one of the waveguide reflectors extend into a portion of the fluid flowing through the pipe. A second acoustic waveguide extends into another portion of the flowing fluid. The second waveguide also has a base segment, and a reflector segment with spaced apart disc shaped reflectors. The reflectors are perpendicular to an axis of the second waveguide reflector segment, and at least one of these waveguide reflectors extend into another portion of the fluid flowing through the pipe, which is a different portion of the fluid flow than the one into which the first acoustic waveguide extends.

In another embodiment, a method is used to determine a location of a fluid layer in a multi-layer fluid flow. An acoustic waveguide with disc shaped acoustic reflectors is extended into the fluid flow and an acoustic wave is propagated through the acoustic waveguide. Echoes of the acoustic wave reflected by the waveguide reflectors are received and a location of the selected fluid layer is determined based on characteristics of the echoes.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
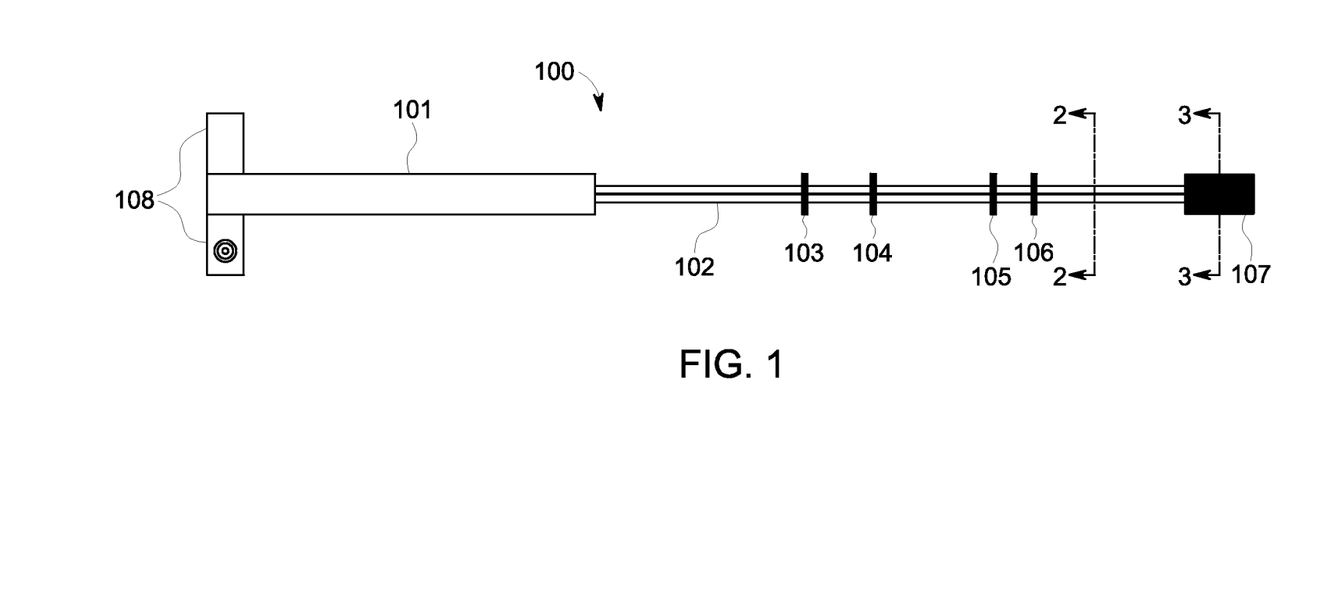
FIG. 1 is a diagram of an acoustic waveguide.
Figure 2:
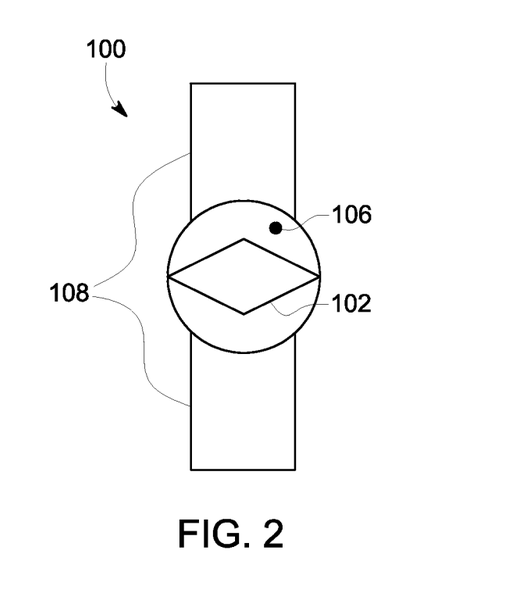
FIG. 2 is a sectional view taken at 2-2 of FIG. 1.
Figure 3:
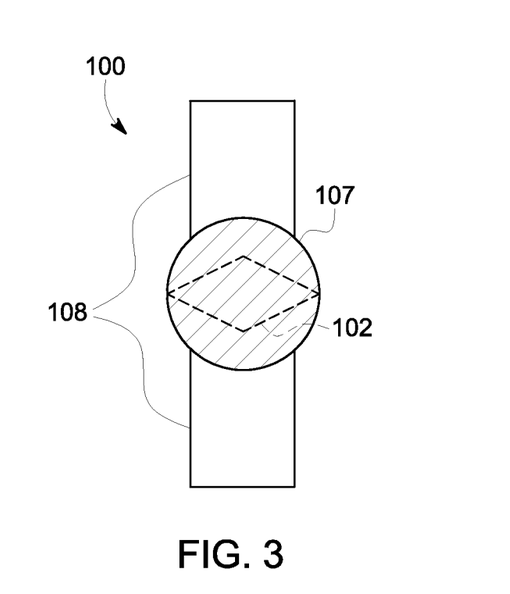
FIG. 3 is a sectional view taken at 3-3 of FIG. 1.

With reference to FIG. 1 there is illustrated an exemplary acoustic waveguide 100 comprising a waveguide base segment 101 at a proximal end of the acoustic waveguide 100, and a waveguide reflector segment 102 at a distal end of the acoustic waveguide 100. FIG. 2 illustrates a substantially parallelogram shaped cross-section through the waveguide reflector segment 102 of the waveguide 100, and FIG. 3 illustrates a circular cross-section through thick waveguide reflector 107. The waveguide reflector segment 102 comprises a plurality of disc shaped waveguide reflectors 103-106. Each of the waveguide reflectors 103-106 is disposed in a plane perpendicular to a lengthwise axis of the acoustic waveguide 100. A thickness of each of the waveguide reflectors 103-106 is less than the aforementioned thick waveguide reflector 107, as measured parallel to the lengthwise axis of the acoustic waveguide 100. Each of the waveguide reflectors 103-106 comprises a thickness of approximately 1.0 mm and comprises a circular cross-section, as is illustrated by waveguide reflector 106 seen in FIG. 2. The thick waveguide reflector 107 comprises a thickness of between about 10.0 mm and about 25.0 mm. The waveguide reflectors 103-106 may or may not be spaced apart uniformly or symmetrically. As illustrated in FIG. 1, the waveguide reflectors 103-106 are not spaced apart uniformly or symmetrically. The thick waveguide reflector 107 may be disposed at the distal end of the waveguide reflector segment 102, as illustrated in FIG. 1, or it may be disposed in another location of the waveguide reflector segment 102. A diameter of the waveguide reflectors 103-107, as measured in cross-section, may range from about 0.25 inch to about 1 inch. The diameter of the waveguide reflectors 103-107 can be equal to each other and to a diameter of the waveguide base segment 101. In one embodiment, the waveguide base segment 101 comprises a cross-section diameter different from the waveguide reflectors 103-107. In another embodiment, the reflector segment 102 of the acoustic waveguide 100 may comprise a length of between about 3 feet and about 10 feet. Thus, a total thickness of waveguide reflectors 103-107 may comprise a small percentage of the length of a three foot long reflector segment 102.

The acoustic waveguide 100 is typically fabricated from a rigid metal rod, such as stainless steel or titanium, of substantially circular cross-section and is machined, but for the waveguide reflectors 103-107, such as by grinding or milling, for example, to achieve the parallelogram shaped cross-section of the waveguide reflector segment 102 having the waveguide reflectors 103-107 integrally formed along with the parallelogram shaped cross-section. The waveguide reflector segment 102 comprises a portion of the acoustic waveguide 100 that is submerged in a fluid flow to detect different fluid layers therein, as described in detail below.

In one embodiment, a transducer assembly 108 is coupled to the proximal end of the acoustic waveguide 100. The transducer assembly 108 can comprise two transducers on opposite sides of the waveguide base segment 101 and be configured to launch an ultrasonic wave into the acoustic waveguide 100 and to detect ultrasonic waves reflected back from each of the waveguide reflectors 103-107. The reflected ultrasonic waves are typically referred to as echoes herein. Each of the transducers may comprise an ultrasonic transducer having a piezoelectric crystal encapsulated by packaging, or in another embodiment, only comprise the piezoelectric crystal. The transducer assembly 108 is coupled to the circumference of the waveguide base segment 101. The transducer assembly 108 can be coupled to the waveguide base segment 101 using, e.g., an adhesive (epoxy) or a circumferential clamp. An output of the transducer assembly 108 is electrically connected to a processing system (not shown) which receives electrical signals representing the detected ultrasonic echoes and processes the signals to calculate times-of-flight of the ultrasonic echoes, which is a function of the speed of the ultrasonic waves traveling through the acoustic waveguide 100, and to display amplitudes of the detected echoes in the form of electronic waveforms on a monitor, as described below.

In different embodiments, the mounting locations of the transducers on the acoustic waveguide 100, mounting angles of the transducers with respect to the longitudinal axis of the acoustic waveguide 100, polarity of the transducers, and the electrical excitation pulse received by the transducers from the processing system can be modified to launch particular acoustic waves, or pulses, (e.g., ultrasonic torsional, extensional, flexural waves) into the acoustic waveguide 100. Although the exemplary acoustic waveguides 100 and 110 (FIG. 6) disclosed herein will be described with respect to use with torsional waves, it will be understood that the waveguides 100, 110 can be used for different acoustic waves.

An ultrasonic torsional wave is a wave motion in which the vibrations of the medium are periodic twisting motions around the direction of propagation along the lengthwise axis of the acoustic waveguide 100. For use with torsional waves, the acoustic waveguide 100 can comprise 0.25 in. diameter (6.35 mm) waveguide reflectors 103-107 for a 100 kHz wave; 0.375 in. diameter (9.53 mm) waveguide reflectors 103-107 for a 75 kHz wave; 0.50 in. diameter (12.70 mm) waveguide reflectors 103-107 for a 50 kHz wave, and even greater diameters. The diameter of the base segment 101 of the acoustic waveguide 100 and of the waveguide reflectors 103-107 may also be selected according to a length of the acoustic waveguide 100 which may require the added rigidity of a larger diameter rod.

When the ultrasonic torsional wave traveling down the acoustic waveguide 100 impacts waveguide reflectors 103-107, the ultrasonic torsional wave is partially reflected by the waveguide reflectors 103-107 back to the transducer assembly 108 enabling the processing system to calculate times-of-flight for each of the waveguide reflectors 103-107, i.e., determined by the speed of the ultrasonic torsional wave, based on the time of a detected peak in the reflection occurring during a programmed time window. As an example, a portion of the torsional ultrasonic wave is reflected by a first one of the waveguide reflectors 103 while the remainder of the ultrasonic torsional wave continues propagating through the waveguide reflector segment 102 and causes the other waveguide reflectors 104-107 to likewise generate reflected echoes traveling back through the acoustic waveguide 100 to the transducer assembly 108, which are detected thereby. With respect to the thick waveguide reflector 107, a front, proximal face of the thick waveguide reflector 107 reflects the ultrasonic torsional wave as well as the back, distal face of the thick waveguide reflector 107. When the remainder of the ultrasonic torsional wave reaches the end of the acoustic waveguide 100, which is the back face of thick waveguide reflector 107 in the example embodiment of FIG. 1, the ultrasonic torsional wave will reflect back to the transducer assembly 108, thereby providing another time-of-flight measurement for the acoustic waveguide 100 end point.

Figure 4:
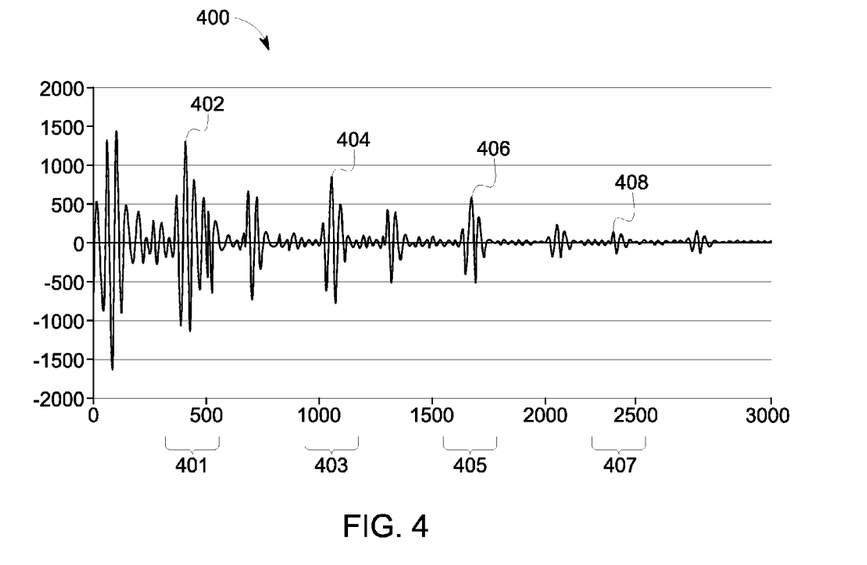
FIG. 4 is a readout of acoustic echoes detected by the waveguide of FIG. 1 while submerged in a known homogeneous fluid.

With reference to FIG. 4 there is illustrated an example echo waveform 400, detected by transducer assembly 108, of a reflected ultrasonic torsional wave from waveguide reflectors 103-106. The illustrated waveform is electronically displayed on a monitor of the processing system, electrically connected to the transducer assembly 108, which receives electrical signals from the transducer assembly 108 that are generated in response to the transducer assembly 108 detecting the ultrasonic echoes. The waveforms enable time-of-flight measurements corresponding to each of the waveguide reflectors 103-106. In the example echo waveform 400 of FIG. 4, the waveguide reflectors 103-106 are submerged in a reference homogeneous fluid, such as water, and generate ultrasonic echoes having known times-of-flight. The four echoes, one from each of the four waveguide reflectors 103-106, comprise, in decreasing amplitude, first echo 402, second echo 404, third echo 406, and fourth echo 408. These are detected during four programmed time windows comprising first time window 401, second time window 403, third time window 405, and fourth time window 407, respectively, and correspond to the echoes reflected from the four waveguide reflectors 103, 104, 105, and 106, respectively. Each of the four waveguide reflectors 103-106 reflect the same ultrasonic wave launched from transducer assembly 108. Each waveguide reflector 103-106 that is further from the transducer assembly 108 reflects a weaker echo detected by the transducer assembly 108, as illustrated by its smaller amplitude, due to the greater distance that the outgoing wave and the reflected echo must travel which diffuses more energy from the ultrasonic wave as compared to a shorter transit route. Echoes reflected by the front and back faces of thick waveguide reflector 107 (not shown), as described above, are similarly detected by transducer assembly 108 as a pair of echoes.

The shape of the reflector segment cross-section 107 between each of the waveguide reflectors 103-106 is a parallelogram, or diamond. This shape is known to cause a detectable reaction that is affected by the density of fluid in which it is submerged when a torsional ultrasonic wave impacts a waveguide reflector 103-106. The density of the fluid causes known characteristic changes to the time-of-flight of reflected echoes which correspond to the density of the fluid layer that the waveguide reflector 103-106 is submerged in. The shape of the cross-section of the thick waveguide reflector 107, which is circular, is less sensitive to fluid density changes than the parallelogram shaped cross-section. However, the circular cross-section of the thick waveguide reflector 107 remains sensitive to temperature changes of the fluid in which it is submerged, and so can be used for temperature measurement, for detecting temperature changes, and temperature calibration and compensation of the acoustic waveguide 100. The thick waveguide reflector 107 is utilized in this manner by measuring a difference in times-of-flight as between echoes reflected from its front and back faces. This time-of-flight delta corresponds to known temperatures and can be used as an index into a lookup table to determine a corresponding temperature of the waveguide reflector 107, for temperature compensation purposes. In one embodiment, the diameter of the thick waveguide reflector 107 is smaller than the diameters of reflectors 103-106 such that a cross-sectional area of the thick waveguide reflector 107 is substantially equal to the parallelogram shaped cross-sectional area of the waveguide reflector segment 102.

Figure 5:
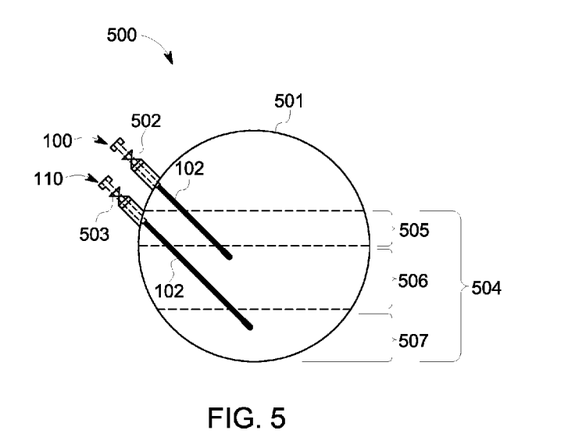
FIG. 5 is a diagram of a fluid flow detection system.

With reference to FIG. 5, there is illustrated a fluid flow system 500 wherein a pipe 501 contains a fluid flow 504 traveling therethrough at a certain depth. The fluid flow 504 depth is separated into layers, e.g. 505, 506, and 507, according to a density of each of the layers 505-507 under influence of gravity. Acoustic waveguides 100, 110 are mounted on the pipe using waveguide mounts 502, 503, respectively, and at least a portion of the waveguide reflector segments 102 from each acoustic waveguide 100, 110 is submerged in the fluid flow. At least one of the waveguide reflectors 103-106 of acoustic waveguide 100 is not submerged in fluid flow layer 506 and at least one of its waveguide reflectors 103-106 is submerged in the fluid flow layer 506. The waveguide reflectors 103-106 submerged in the fluid flow 504 will each reflect an echo having a time-of-flight. The times-of-flight are used to determine a density of the fluid layer in which a particular waveguide reflector 103-106 is submerged. Such a determination is obtained, for example, using a table listing densities correlated to each time-of-flight.

With respect to acoustic waveguide 110, at least one of the waveguide reflectors 103-106 of acoustic waveguide 110 is submerged in each of the fluid flow layers 506 and 507. Using the known locations of the waveguide reflectors 103-106 along the lengths of the reflector segments 102, the depths of the fluid flow layers 506 and 507 can be determined the times-of-flight generated by waveguide reflectors 103-106 of acoustic waveguide 110 submerged therein.

Although FIG. 5 shows the exemplary acoustic waveguides 100, 110 mounted to a pipe, it will be understood that the acoustic waveguides 100, 110 can be mounted to a variety of conduits by which fluid is contained (e.g., a pipe, tube, vessel, tank, etc.). FIG. 5 also shows that acoustic waveguide 110 comprises a longer waveguide reflector segment 102 than acoustic waveguide 100. In one embodiment, the acoustic waveguides 100, 110 may comprise reflector segments 102 of similar length but are mounted at different locations on pipe 501 to detect different fluid flow layers in the fluid flow 504. In another embodiment, the lengths of reflector segments 102 of acoustic waveguides 100, 110 may be similar but the waveguide reflectors 103-106 of acoustic waveguide 100 may be disposed proximal to its base segment 101, and the waveguide reflectors 103-106 of acoustic waveguide 110 may be disposed distal to its base segment 101. The number and separation distances of waveguide reflectors 103-107, as well as an overall length of acoustic waveguides 100, 110 may be configured in a variety of combinations according to dimensions of fluid conduits and containers, and according to compositions of fluids to be measured. The scope of the claims recited hereunder are not intended to be limited to any particular one of such configurations.

Figure 6:
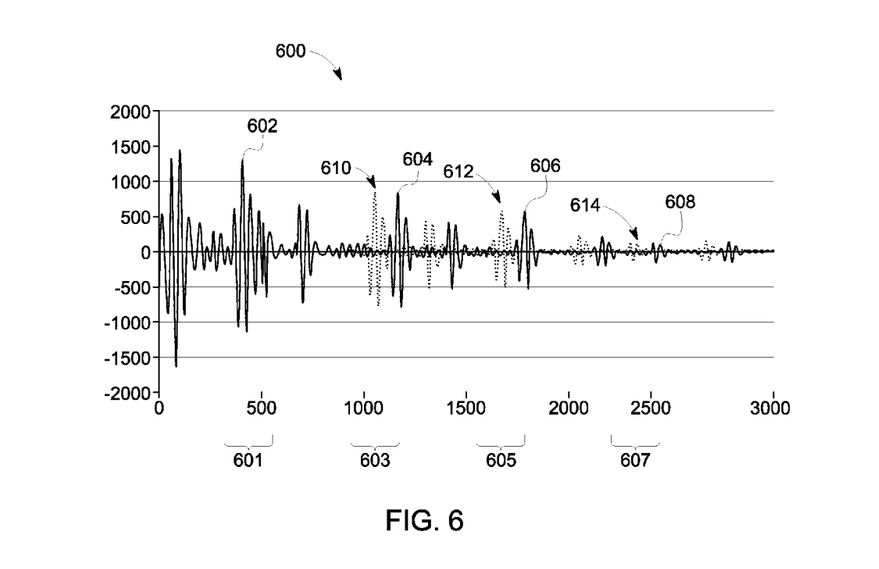
FIG. 6 is a waveform of acoustic echoes detected by the acoustic waveguide of FIG. 1 while submerged in a multi-layer fluid flow.

With reference to FIG. 6 there is illustrated an example echo waveform 600 detected by transducer assembly 108 of an ultrasonic torsional wave that is reflected by waveguide reflectors 103-106 of an acoustic waveguide 100 submerged in a pipe, such as pipe 501, having a multi-layered fluid traveling therethrough. For example, a fluid flow comprising at least water and oil will separate into layers due to their different densities and the effects of gravity thereon. As before, four echo waveforms, comprising first reference echo 602, second reference echo 604, third reference echo 606, and fourth reference echo 608, represent times-of-flight of known reference fluids in which the acoustic waveguide is submerged, as described above with respect to FIG. 4. These are used as reference points to programmably situate four time windows, comprising first time window 601, second time window 603, third time window 605, and fourth time window 607, respectively, which correspond to the four waveguide reflectors 103, 104, 105, 106, respectively, to detect echoes reflected thereby. The actual detected echoes 610, 612, 614 during time windows 603, 605, and 607, respectively, corresponding to waveguide reflectors 104, 105, 106, respectively, precede the expected standard reference echoes 604, 606, and 608, respectively, i.e. are faster and have a shorter time-of-flight.

The detected echo reflected by waveguide reflector 103 during time window 601 does not indicate a time-of-flight deviation from the first reference echo 602, thus, it indicates that waveguide reflector 103 is not submerged in a fluid layer having a density different from the reference fluid, e.g. water. These detected echoes altogether indicate that the upper border of a fluid flow layer heavier than water is located between waveguide reflectors 103 and 104. Similarly, the location of a bottom border of a fluid layer can be determined using the same acoustic waveguide 100, or a combination of acoustic waveguides 100 and 110 such as in the embodiment of FIG. 5. The known positions of the waveguide reflectors 103-106 along an acoustic waveguide 100 can thereby be used to determine the depth of fluid layers having different densities in the fluid flowing through a pipe. Such information may be used to control a volume of the fluid flow so as to control separation or depth of the layers in the fluid flow. Maximum separation may be desirable to enable drawing off an oil layer, for example.

In one embodiment, referring now to FIG. 5, fluid layer 507 may comprise oil while fluid layer 505 may comprise water. Fluid layer 506 may comprise an emulsion of water and oil, i.e. a "rag layer". Determining the location of the rag layer may be used to assist a more efficient drawing off of water and/or oil downstream of the acoustic waveguide mounting location. The size, i.e. top to bottom depth, of the rag layer may be determined in order to employ means for reducing a size of the rag layer, such as by adjusting a flow rate of the overall fluid volume, or such information may be used to properly situate means for siphoning the oil and/or water from the fluid flow.

In view of the foregoing, embodiments of the invention provide a measurement device, system, and method to determine depths of various fluids flowing through a pipe. A technical effect is to accurately locate fluid layers in a fluid flow.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "processing system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An elongated acoustic waveguide comprising:
    a waveguide base segment;
    a waveguide reflector segment; and
    the waveguide reflector segment comprising a plurality of
        disc shaped waveguide reflectors spaced apart along its length, each of the waveguide reflectors disposed in a plane perpendicular to an axis of the waveguide reflector segment,
wherein the waveguide reflector segment comprises a substantially circular cross-section and a parallelogram shaped cross-section, the substantially circular cross-section positioned at a location of each waveguide reflector and the parallelogram shaped cross-section positioned within each of the waveguide reflectors.

2. The acoustic waveguide according to claim 1, wherein one of the waveguide reflectors comprises a thickness, measured parallel to the axis of the waveguide reflector segment, between about ten times to about twenty-five times a thickness of at least one of the other waveguide reflectors.

3. The acoustic waveguide according to claim 2, wherein the one of the waveguide reflectors is disposed at a distal end of the waveguide reflector segment.

4. The acoustic waveguide according to claim 1, wherein the waveguide base segment and the disc shaped waveguide reflectors comprise a substantially circular cross-section of substantially equal diameter.

5. The acoustic waveguide according to claim 4, wherein a remainder of the waveguide reflector segment comprises a substantially parallelogram shaped cross-section.

6. The acoustic waveguide according to claim 2, further comprising:
an ultrasonic transducer acoustically coupled to the waveguide base segment for launching an ultrasonic pulse into the acoustic waveguide, and for receiving echoes of the ultrasonic wave reflected from the waveguide reflectors.

7. The acoustic waveguide according to claim 6, wherein the one of the waveguide reflectors comprises an end proximal to the ultrasonic transducer and an end distal to the ultrasonic transducer, and reflects the ultrasonic wave at its proximal end and at its distal end.

8. The acoustic waveguide according to claim 7, wherein the one of the waveguide reflectors generates a reflected pair of ultrasonic echoes corresponding to the proximal end and the distal end, the pair of ultrasonic echoes comprising a speed corresponding to a temperature of the one of the waveguide reflectors.

9. A fluid flow system having a pipe with fluid flowing therethrough, the system comprising:
a first acoustic waveguide with a first waveguide base segment and a first waveguide reflector segment, the first waveguide reflector segment comprising a first plurality of disc shaped waveguide spaced apart along a portion of its length, each of the first plurality of waveguide reflectors disposed in a plane perpendicular to an axis of the first waveguide reflector segment, at least one of the first plurality of waveguide reflectors extending into a first portion of the fluid flowing through the pipe;
a second acoustic waveguide with a second waveguide base segment and a second waveguide reflector segment, the second waveguide reflector segment comprising a second plurality of disc shaped waveguide reflectors spaced apart along a portion of its length, each of the second plurality of waveguide reflectors disposed in a plane perpendicular to an axis of the second waveguide reflector segment, at least one of the second plurality of waveguide reflectors extending into a second portion of the fluid flowing through the pipe, wherein the second portion of the fluid is different than the first portion of fluid,
wherein the first and second pluralities of waveguide reflector segments each comprise a substantially circular cross-section and a substantially parallelogram shaped cross-section, the substantially circular cross-sections positioned at locations of each of the first and second plurality of waveguide reflectors and the substantially parallelogram shaped cross-section positioned within each of the waveguide reflectors.

10. The fluid flow system of claim 9, wherein the second waveguide reflector segment is longer than the first waveguide reflector segment.

11. The fluid flow system of claim 9, wherein the first waveguide reflector segment and the second waveguide reflector segment comprise equal lengths and wherein the second plurality of waveguide reflectors are located in a portion of the second waveguide reflector segment further from the second waveguide base segment than the first plurality of waveguide reflectors are located from the first waveguide base segment.

12. The fluid flow system according to claim 9, further comprising:
a first ultrasonic transducer acoustically coupled to the first waveguide base segment for transmitting a first ultrasonic wave into the first waveguide base segment, and for receiving echoes of the first ultrasonic wave reflected from the first plurality of waveguide reflectors; and
a second ultrasonic transducer acoustically coupled to the second waveguide base segment for transmitting a second ultrasonic wave into the second waveguide base segment, and for receiving echoes of the second wave reflected from the second plurality of waveguide reflectors.

13. The fluid flow system according to claim 9, wherein one of the first plurality of waveguide reflectors comprises a thickness, measured parallel to the axis of the first waveguide reflector segment, between about ten times to about twenty five times a thickness of at least one other of the first plurality of waveguide reflectors, and wherein one of the second plurality of waveguide reflectors comprises a thickness, measured parallel to the axis of the second waveguide reflector segment, between about ten times to about twenty five times a thickness of at least one other of the second plurality of waveguide reflectors.

14. The fluid flow system according to claim 13, wherein the one of the first plurality of waveguide reflectors and the one of the second plurality of waveguide reflectors each comprises an end proximal to its corresponding ultrasonic transducer and an end distal to the corresponding ultrasonic transducer, and wherein each of the proximal ends and each of the distal ends reflects its corresponding ultrasonic wave.

15. The fluid flow system according to claim 14, wherein the one of the first plurality of waveguide reflectors and the one of the second plurality of waveguide reflectors each generate a reflected pair of ultrasonic echoes corresponding to its proximal end and its distal end, each pair of ultrasonic echoes comprising characteristics corresponding to a temperature of the waveguide reflector that generated it.

16. A method of determining a location of a selected fluid layer in a fluid flow wherein the fluid flow comprises a plurality of flowing layers, the method comprising:
extending an acoustic waveguide into the fluid flow, the acoustic waveguide comprising a first plurality of disc shaped acoustic waveguide reflectors spaced along a waveguide reflector segment, wherein the waveguide reflector segment comprises a substantially circular cross-section positioned at a location of each waveguide reflector and a parallelogram shaped cross-section positioned within each of the waveguide reflectors;

propagating an acoustic wave through the acoustic waveguide;

receiving echoes of the acoustic wave reflected by the waveguide reflectors; and determining a location of the selected fluid layer based on characteristics of the echoes.

17. The method of claim 16, wherein the step of determining comprises measuring a time-of-flight of the received echoes reflected by different ones of the waveguide reflectors.

18. The method of claim 16, further comprising:

extending a second acoustic waveguide into the fluid flow, the second acoustic waveguide comprising a second plurality of disc shaped acoustic waveguide reflectors, the second plurality of waveguide reflectors extending further into the fluid flow than the first plurality of waveguide reflectors;

propagating an acoustic wave through the second acoustic waveguide;

receiving echoes of the acoustic wave reflected by the second plurality of waveguide reflectors; and determining the location of the selected fluid layer based on characteristics of the echoes reflected by the second plurality of waveguide reflectors.

* * * * *